United States Patent
Farwick et al.

(10) Patent No.: US 6,921,651 B2
(45) Date of Patent: Jul. 26, 2005

(54) PROCESS FOR THE PREPARATION OF AMINO ACIDS BY USING CORYNEFORM BACTERIA WITH ATTENUATED 1-PHOSPHOFRUCTOKINASE ACTIVITY

(75) Inventors: Mike Farwick, Bielefeld (DE); Brigitte Bathe, Salzkotten (DE); Jennifer Brehme, Bielefeld (DE); Klaus Huthmacher, Gelnhausen (DE)

(73) Assignee: Degussa AG, Düsseldorf (DE)

( * ) Notice: Subject to any disclaimer, the term of this patent is extended or adjusted under 35 U.S.C. 154(b) by 275 days.

(21) Appl. No.: 10/098,626

(22) Filed: Mar. 18, 2002

(65) Prior Publication Data

US 2003/0092137 A1 May 15, 2003

(30) Foreign Application Priority Data

Mar. 17, 2001 (DE) .......................... 101 12 992

(51) Int. Cl.[7] .............................. C12P 13/04
(52) U.S. Cl. ...................... 435/106; 435/115
(58) Field of Search ................ 435/106, 115

(56) References Cited

U.S. PATENT DOCUMENTS 6,465,238 B1 * 10/2002 Hanke ..................... 435/234

FOREIGN PATENT DOCUMENTS

| DE | 10135051 A1 * | 2/2003 | ........... C12P/13/04 |
|---|---|---|---|
| EP | 1 103 613 A | 5/2001 | |
| EP | 1 106 622 A | 6/2001 | |
| EP | 1 108 790 A2 | 6/2001 | |
| JP | 63 102692 A | 5/1988 | |
| WO | WO 00/77172 A1 | 12/2000 | |

* cited by examiner

Primary Examiner—Kathleen Kerr
(74) Attorney, Agent, or Firm—Smith, Gambrell & Russell

(57) ABSTRACT

The invention relates to a process for the preparation of L-amino acids. The process includes fermenting the coryneform bacteria producing the desired L-amino acid, in which at least the gene coding for 6-phosphofructokinase and/or the gene coding for 1-phosphofructokinase are/is attenuated, enriching the desired L-amino acid in the medium or in the cells of the bacteria, and isolating the L-amino acid. Optionally bacteria are employed in which, in addition, further genes of the biosynthetic pathway of the desired L-amino acid are enhanced, or bacteria are employed in which the metabolic pathways that diminish the formation of the desired L-amino acid are at least partly switched off.

9 Claims, 2 Drawing Sheets

Figure 1: Plasmid pXK99Emob
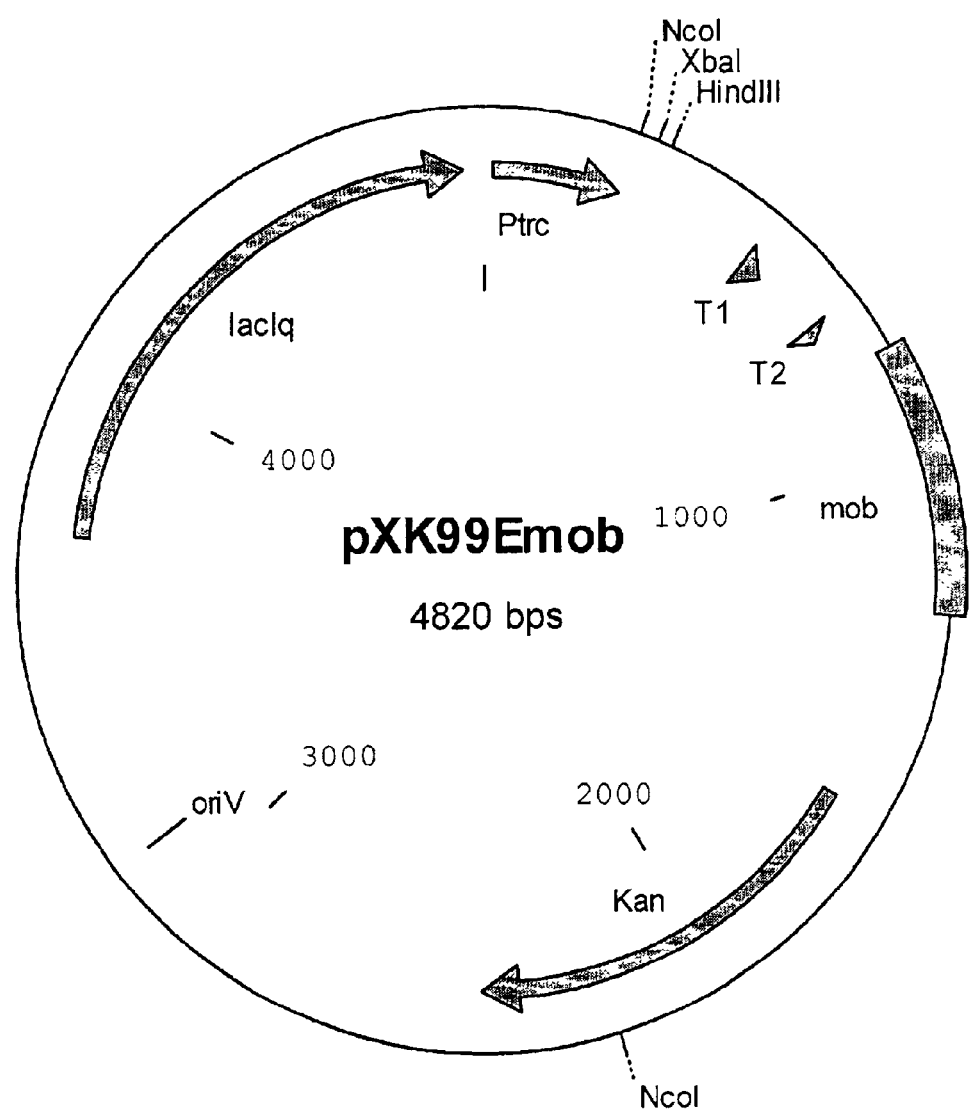

Figure 2: pXK99EmobpfkB
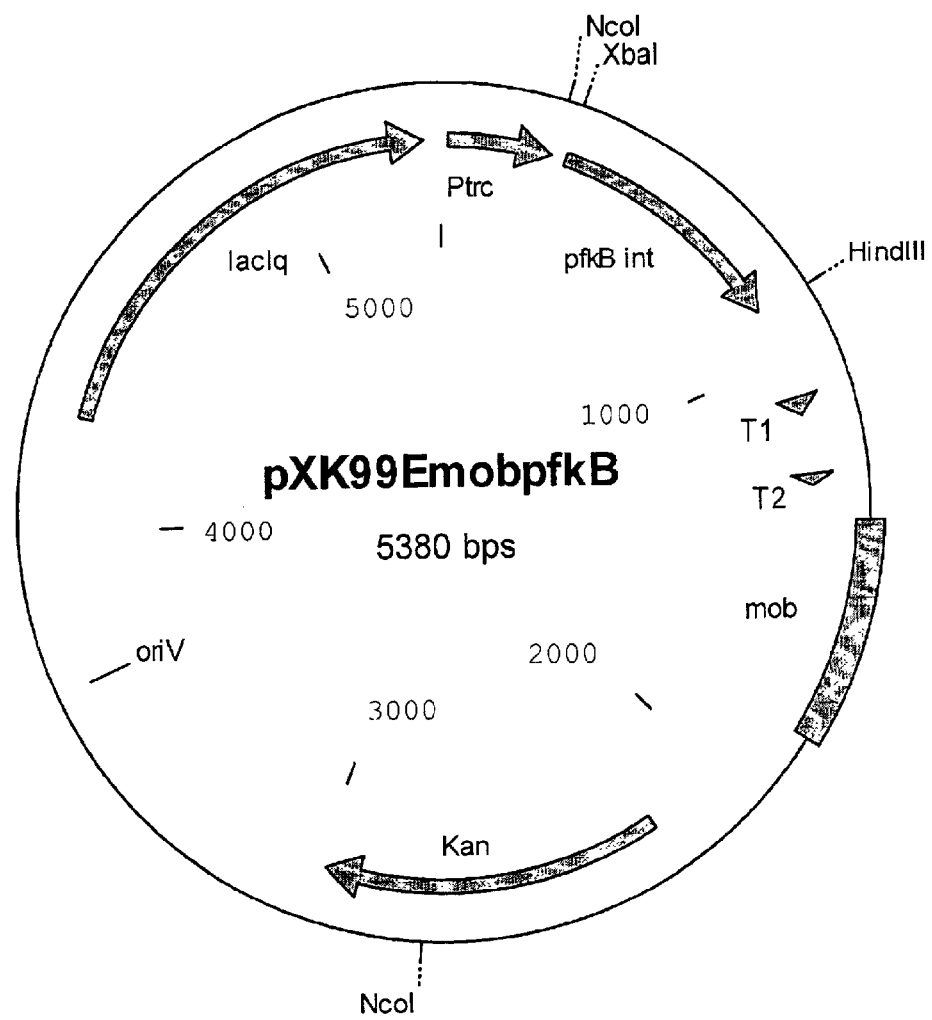

SEQUENCE LISTING

```
<160> NUMBER OF SEQ ID NOS: 6

<210> SEQ ID NO 1
<211> LENGTH: 2234
<212> TYPE: DNA
<213> ORGANISM: Corynebacterium glutamicum
<220> FEATURE:
<221> NAME/KEY: CDS
<222> LOCATION: (632)..(1660)
<223> OTHER INFORMATION:

<400> SEQUENCE: 1
cctctaataa gagtcgcccc gataagtttt tttaccgtaa ttattactgg gagtcagata      60
ctgcgtaagc aatcgcagca gcgccagcgg tcacagtaag aactgcaggc cacgcgccaa     120
tcttcttggc aagtgggtgg gacaggccaa atgcaccaac gtaggttgcc agcaggccag     180
tagctactgc aggacccttc ttttcattcc agcttcgtgc agcaagcgct ccggatgctg     240
ccaatggaat ggtgcccagt gggcgaatgc cggattcacg ggcagtcaac caaccgccga     300
tcaaacctgc tgcgacgacg gtggcagtgc tgacctggga tgccttttc aatttcattt      360
```

-continued

| | |
|---|---|
| ccatggtgag ccagtctaga gacaaaattt ttccgcgggg gttttcttga tctgatccga | 420 |
| caacccaatg ggggcaaaaa tgtgtccgac caaaaattgt gcagcacacc acatgcccgc | 480 |
| tcggacaatg tcgatttgtt aatgaaactg cagctctggc gattaaataa gatggtcaga | 540 |
| gacagttttt tggcctgtca acccctgtga ttctcttatt tttgggtgat tgttccggcg | 600 |
| cgggtgttgt gatgggttta atatggaaga c atg cga att gct act ctc acg | 652 |

```
                                       Met Arg Ile Ala Thr Leu Thr
                                        1               5 tca ggc ggc gac tgc ccc gga cta aac gcc gtc atc cga gga atc gtc    700
Ser Gly Gly Asp Cys Pro Gly Leu Asn Ala Val Ile Arg Gly Ile Val
         10              15                  20 cgc aca gcc agc aat gaa ttt ggc tcc acc gtc gtt ggt tat caa gac    748
Arg Thr Ala Ser Asn Glu Phe Gly Ser Thr Val Val Gly Tyr Gln Asp
     25                  30                  35 ggt tgg gaa gga ctg tta ggc gat cgt cgc gta cag ctg tat gac gat    796
Gly Trp Glu Gly Leu Leu Gly Asp Arg Arg Val Gln Leu Tyr Asp Asp
 40              45                  50                  55 gaa gat att gac cga atc ctc ctt cga ggc ggc acc att ttg ggc act    844
Glu Asp Ile Asp Arg Ile Leu Leu Arg Gly Gly Thr Ile Leu Gly Thr
                     60                  65                  70 ggt cgc ctc cat ccg gac aag ttt aag gcc gga att gat cag att aag    892
Gly Arg Leu His Pro Asp Lys Phe Lys Ala Gly Ile Asp Gln Ile Lys
                 75                  80                  85 gcc aac tta gaa gac gcc ggc atc gat gcc ctt atc cca atc ggt ggc    940
Ala Asn Leu Glu Asp Ala Gly Ile Asp Ala Leu Ile Pro Ile Gly Gly
             90                  95                 100 gaa gga acc ctg aag ggt gcc aag tgg ctg tct gat aac ggt atc cct    988
Glu Gly Thr Leu Lys Gly Ala Lys Trp Leu Ser Asp Asn Gly Ile Pro
        105                 110                 115 gtt gtc ggt gtc cca aag acc att gac aat gac gtg aat ggc act gac   1036
Val Val Gly Val Pro Lys Thr Ile Asp Asn Asp Val Asn Gly Thr Asp
120                 125                 130                 135 ttc acc ttc ggt ttc gat act gct gtg gca gtg gct acc gac gct gtt   1084
Phe Thr Phe Gly Phe Asp Thr Ala Val Ala Val Ala Thr Asp Ala Val
                140                 145                 150 gac cgc ctg cac acc acc gct gaa tct cac aac cgt gtg atg atc gtg   1132
Asp Arg Leu His Thr Thr Ala Glu Ser His Asn Arg Val Met Ile Val
            155                 160                 165 gag gtc atg ggc cgc cac gtg ggt tgg att gct ctg cac gca ggt atg   1180
Glu Val Met Gly Arg His Val Gly Trp Ile Ala Leu His Ala Gly Met
        170                 175                 180 gcc ggc ggt gct cac tac acc gtt att cca gaa gta cct ttc gat att   1228
Ala Gly Gly Ala His Tyr Thr Val Ile Pro Glu Val Pro Phe Asp Ile
185                 190                 195 gca gag atc tgc aag gcg atg gaa cgt cgc ttc cag atg ggc gag aag   1276
Ala Glu Ile Cys Lys Ala Met Glu Arg Arg Phe Gln Met Gly Glu Lys
200                 205                 210                 215 tac ggc att atc gtc gtt gcg gaa ggt gcg ttg cca cgc gaa ggc acc   1324
Tyr Gly Ile Ile Val Val Ala Glu Gly Ala Leu Pro Arg Glu Gly Thr
                220                 225                 230 atg gag ctt cgt gaa ggc cac att gac cag ttc ggt cac aag acc ttc   1372
Met Glu Leu Arg Glu Gly His Ile Asp Gln Phe Gly His Lys Thr Phe
            235                 240                 245 acg gga att gga cag cag atc gct gat gag atc cac gtg cgc ctc ggc   1420
Thr Gly Ile Gly Gln Gln Ile Ala Asp Glu Ile His Val Arg Leu Gly
        250                 255                 260 cac gat gtt cgt acg acc gtt ctt ggc cac att caa cgt ggt gga acc   1468
His Asp Val Arg Thr Thr Val Leu Gly His Ile Gln Arg Gly Gly Thr
265                 270                 275
```

-continued

```
cca act gct ttc gac cgt gtt ctg gcc act cgt tat ggt gtt cgt gca    1516
Pro Thr Ala Phe Asp Arg Val Leu Ala Thr Arg Tyr Gly Val Arg Ala
280                 285                 290                 295 gct cgt gcg tgc cat gag gga agc ttt gac aag gtt gtt gct ttg aag    1564
Ala Arg Ala Cys His Glu Gly Ser Phe Asp Lys Val Val Ala Leu Lys
                300                 305                 310 ggt gag agc att gag atg atc acc ttt gaa gaa gca gtc gga acc ttg    1612
Gly Glu Ser Ile Glu Met Ile Thr Phe Glu Glu Ala Val Gly Thr Leu
            315                 320                 325 aag gaa gtt cca ttc gaa cgc tgg gtt act gcc cag gca atg ttt gga    1660
Lys Glu Val Pro Phe Glu Arg Trp Val Thr Ala Gln Ala Met Phe Gly
        330                 335                 340 tagttttcg gcttttatc aacagccaat aacagctctt tcgcccattg aggtggaggg    1720 gctgttttt catgccgtaa ggaaagtgca agtaagtgaa atcaagtggc ctagatccat    1780
tgacacttag actgtgacct aggcttgact ttcgtggggg agtggggata agttcatctt    1840
aaacacaatg caatcgattg catttacgtt ccttatccca caatagggt accttccaga    1900 aagttggtga ggagatggct tccgaaacct ccagcccgaa gaagcgggcc accacgctca    1960
aagacatcgc gcaagcaaca cagctttcag tcagcacggt gtcccgggca ttggccaaca    2020
acgcgagcat tccggaatcc acacgcatcc gagtggttga agccgctcaa aagctgaact    2080
accgtcccaa tgcccaagct cgtgcattgc ggaagtcgag gacagacacc atcggtgtca    2140
tcattccaaa cattgagaac ccatatttct cctcactagc agcatcgatt caaaaagctg    2200
ctcgtgaagc tggggtgtcc accattttgt ccaa                              2234
```

<210> SEQ ID NO 2
<211> LENGTH: 343
<212> TYPE: PRT
<213> ORGANISM: Corynebacterium glutamicum

<400> SEQUENCE: 2

```
Met Arg Ile Ala Thr Leu Thr Ser Gly Gly Asp Cys Pro Gly Leu Asn
1               5                   10                  15

Ala Val Ile Arg Gly Ile Val Arg Thr Ala Ser Asn Glu Phe Gly Ser
                20                  25                  30

Thr Val Val Gly Tyr Gln Asp Gly Trp Glu Gly Leu Leu Gly Asp Arg
            35                  40                  45

Arg Val Gln Leu Tyr Asp Asp Glu Asp Ile Asp Arg Ile Leu Leu Arg
        50                  55                  60

Gly Gly Thr Ile Leu Gly Thr Gly Arg Leu His Pro Asp Lys Phe Lys
65                  70                  75                  80

Ala Gly Ile Asp Gln Ile Lys Ala Asn Leu Glu Asp Ala Gly Ile Asp
                85                  90                  95

Ala Leu Ile Pro Ile Gly Gly Glu Gly Thr Leu Lys Gly Ala Lys Trp
            100                 105                 110

Leu Ser Asp Asn Gly Ile Pro Val Val Gly Val Pro Lys Thr Ile Asp
        115                 120                 125

Asn Asp Val Asn Gly Thr Asp Phe Thr Phe Gly Phe Asp Thr Ala Val
    130                 135                 140

Ala Val Ala Thr Asp Ala Val Asp Arg Leu His Thr Thr Ala Glu Ser
145                 150                 155                 160

His Asn Arg Val Met Ile Val Glu Val Met Gly Arg His Val Gly Trp
                165                 170                 175

Ile Ala Leu His Ala Gly Met Ala Gly Gly Ala His Tyr Thr Val Ile
```

-continued

```
                    180                 185                 190
Pro Glu Val Pro Phe Asp Ile Ala Glu Ile Cys Lys Ala Met Glu Arg
        195                 200                 205

Arg Phe Gln Met Gly Glu Lys Tyr Gly Ile Ile Val Val Ala Glu Gly
    210                 215                 220

Ala Leu Pro Arg Glu Gly Thr Met Glu Leu Arg Glu Gly His Ile Asp
225                 230                 235                 240

Gln Phe Gly His Lys Thr Phe Thr Gly Ile Gly Gln Gln Ile Ala Asp
                245                 250                 255

Glu Ile His Val Arg Leu Gly His Asp Val Arg Thr Thr Val Leu Gly
            260                 265                 270

His Ile Gln Arg Gly Gly Thr Pro Thr Ala Phe Asp Arg Val Leu Ala
        275                 280                 285

Thr Arg Tyr Gly Val Arg Ala Ala Arg Ala Cys His Glu Gly Ser Phe
    290                 295                 300

Asp Lys Val Val Ala Leu Lys Gly Glu Ser Ile Glu Met Ile Thr Phe
305                 310                 315                 320

Glu Glu Ala Val Gly Thr Leu Lys Glu Val Pro Phe Glu Arg Trp Val
                325                 330                 335

Thr Ala Gln Ala Met Phe Gly
            340
```

<210> SEQ ID NO 3
<211> LENGTH: 2160
<212> TYPE: DNA
<213> ORGANISM: Corynebacterium glutamicum
<220> FEATURE:
<221> NAME/KEY: CDS
<222> LOCATION: (609)..(1598)
<223> OTHER INFORMATION:

<400> SEQUENCE: 3

```
cccatgggta cgtctccccc tcggctgaaa cctgccttgg ttaaaggaat gccaccggaa    60
ccccgtgttt tagaacttgc agaaactgca gtttccctca tcacacctct agcacgcagc   120
attttcctgg attcaggttt agcgtgcacg gcgattgcca cggtgttggg ggatcctcca   180
gaagatgcca ggtggactgt tgttacaagt tcccccggcg ctgtgattgc cttgtccgcg   240
acagatgcca cctccacggt ggtgctgcac gggcaggttc acggtaattg ttcttcaatc   300
attgggtcca cggcagtaga catgatttcg cagttgcgcg ctgatatcgc cttcgtggag   360
gttgatgcga ttcaatccga tacaagtctg tgcacgtttt tcccggagac gattcccatc   420
aagcaagcca tgatcaaaaa cgcggctttc acagttgctg ttctcagccc gagatctccc   480
caagatcaag aacttcaact tttgaagcac ccttttccca ccttggctga ttttgatgcc   540
cttgttaccg atgaccacac gctagatttt ccagttttgc ccgaccacaa ctttcaggtg   600 gtaacccc atg atc atc aca ttc acc cca aac ccg agt att gat tcc acg    650
          Met Ile Ile Thr Phe Thr Pro Asn Pro Ser Ile Asp Ser Thr
            1               5                  10 ctg tcg ctc ggc gaa gag ctc tcc cgt gga tcc gtc caa cga ctt gat    698
Leu Ser Leu Gly Glu Glu Leu Ser Arg Gly Ser Val Gln Arg Leu Asp
15                  20                  25                  30 tcc gtc acc gct gtc gca ggt ggt aaa ggc atc aat gtc gcc cac gct    746
Ser Val Thr Ala Val Ala Gly Gly Lys Gly Ile Asn Val Ala His Ala
                35                  40                  45 gtc ttg ctt gcg ggc ttt gaa acc ttg gct gtg ttc cca gcc ggc aag    794
Val Leu Leu Ala Gly Phe Glu Thr Leu Ala Val Phe Pro Ala Gly Lys
            50                  55                  60
```

```
ctc gac ccc ttc gtc cca ctg gtc cgc gac atc ggc ttg ccc gtg gaa      842
Leu Asp Pro Phe Val Pro Leu Val Arg Asp Ile Gly Leu Pro Val Glu
         65                  70                  75 act gtt gtg atc aac aag aac gtc cgc acc aac acc aca gtc acc gaa      890
Thr Val Val Ile Asn Lys Asn Val Arg Thr Asn Thr Thr Val Thr Glu
     80                  85                  90 ccg gac ggc acc acc acc aag ctc aac ggc ccc ggc gcg ccg ctc agc      938
Pro Asp Gly Thr Thr Thr Lys Leu Asn Gly Pro Gly Ala Pro Leu Ser
 95                 100                 105                 110 gag cag aag ctc cgt agc ttg gaa aag gtg ctt atc gac gcg ctc cgc      986
Glu Gln Lys Leu Arg Ser Leu Glu Lys Val Leu Ile Asp Ala Leu Arg
                115                 120                 125 ccc gaa gtc acc tgg gtt gtc ctg gcg ggc tcg ctg cca cca ggg gca     1034
Pro Glu Val Thr Trp Val Val Leu Ala Gly Ser Leu Pro Pro Gly Ala
            130                 135                 140 cca gtt gac tgg tac gcg cgt ctc acc gcg ttg atc cat tca gca cgc     1082
Pro Val Asp Trp Tyr Ala Arg Leu Thr Ala Leu Ile His Ser Ala Arg
        145                 150                 155 cct gac gtt cgc gtg gct gtc gat acc tca gac aag cca ctg atg gcg     1130
Pro Asp Val Arg Val Ala Val Asp Thr Ser Asp Lys Pro Leu Met Ala
    160                 165                 170 ttg ggc gag agc ttg gat aca cct ggc gct gct ccg aac ctg att aag     1178
Leu Gly Glu Ser Leu Asp Thr Pro Gly Ala Ala Pro Asn Leu Ile Lys
175                 180                 185                 190 cca aat ggt ctg gaa ctg ggc cag ctg gct aac act gat ggt gaa gag     1226
Pro Asn Gly Leu Glu Leu Gly Gln Leu Ala Asn Thr Asp Gly Glu Glu
                195                 200                 205 ctg gag gcg cgt gct gcg caa ggc gat tac gac gcc atc atc gca gct     1274
Leu Glu Ala Arg Ala Ala Gln Gly Asp Tyr Asp Ala Ile Ile Ala Ala
            210                 215                 220 gcg gac gta ctg gtt aac cgt ggc atc gaa cag gtg ctt gtc acc ttg     1322
Ala Asp Val Leu Val Asn Arg Gly Ile Glu Gln Val Leu Val Thr Leu
        225                 230                 235 ggt gcc gca gga gcg gtg ttg gtc aac gca gaa ggt gcg tgg act gct     1370
Gly Ala Ala Gly Ala Val Leu Val Asn Ala Glu Gly Ala Trp Thr Ala
    240                 245                 250 act tct cca aag att gat gtt gta tcc acc gtt gga gct gga gac tgt     1418
Thr Ser Pro Lys Ile Asp Val Val Ser Thr Val Gly Ala Gly Asp Cys
255                 260                 265                 270 gct ctt gca ggt ttt gtt atg gca cgt tcc cag aag aaa aca ctg gag     1466
Ala Leu Ala Gly Phe Val Met Ala Arg Ser Gln Lys Lys Thr Leu Glu
                275                 280                 285 gaa tct ctg ctg aat gcc gtg tct tac ggc tcg act gcg gcg tct ctt     1514
Glu Ser Leu Leu Asn Ala Val Ser Tyr Gly Ser Thr Ala Ala Ser Leu
            290                 295                 300 cct ggc act acc att cct cgt cct gac caa ctc gcc aca gct ggt gca     1562
Pro Gly Thr Thr Ile Pro Arg Pro Asp Gln Leu Ala Thr Ala Gly Ala
        305                 310                 315 acg gtc acc caa gtc aaa gga ttg aaa gaa tca gca tgaatagcgt          1608
Thr Val Thr Gln Val Lys Gly Leu Lys Glu Ser Ala
    320                 325                 330 aaataattcc tcgcttgtcc ggctggatgt cgatttcggc gactccacca cggatgtcat   1668
caacaacctt gccactgtta ttttcgacgc tggccgagct tcctccgccg acgcccttgc   1728
caaagacgcg ctggatcgtg aagcaaagtc cggcaccggc gttcctggtc aagttgctat   1788
cccccactgc cgttccgaag ccgtatctgt ccctaccttg gctttgctc gcctgagcaa    1848 gggtgtggac ttcagcggac ctgatggcga tgccaacttg gtgttcctca ttgcagcacc   1908
```

-continued

```
tgctggcggc ggcaaagagc acctgaagat cctgtccaag cttgctcgct ccttggtgaa    1968
gaaggatttc atcaaggctc tgcaggaagc caccaccgag caggaaatcg tcgacgttgt    2028
cgatgccgtg ctcaacccag caccaaaaac caccgagcca gctgcagctc cggctgcggc    2088
ggcggttgct gagagtgggg cggcgtcgac aagcgttact cgtatcgtgg caatcaccgc    2148
atgcccaacc gg                                                        2160
```

<210> SEQ ID NO 4
<211> LENGTH: 330
<212> TYPE: PRT
<213> ORGANISM: Corynebacterium glutamicum

<400> SEQUENCE: 4

Met Ile Ile Thr Phe Thr Pro Asn Pro Ser Ile Asp Ser Thr Leu Ser
1               5                   10                  15

Leu Gly Glu Glu Leu Ser Arg Gly Ser Val Gln Arg Leu Asp Ser Val
            20                  25                  30

Thr Ala Val Ala Gly Gly Lys Gly Ile Asn Val Ala His Ala Val Leu
        35                  40                  45

Leu Ala Gly Phe Glu Thr Leu Ala Val Phe Pro Ala Gly Lys Leu Asp
    50                  55                  60

Pro Phe Val Pro Leu Val Arg Asp Ile Gly Leu Pro Val Glu Thr Val
65                  70                  75                  80

Val Ile Asn Lys Asn Val Arg Thr Asn Thr Thr Val Thr Glu Pro Asp
                85                  90                  95

Gly Thr Thr Thr Lys Leu Asn Gly Pro Gly Ala Pro Leu Ser Glu Gln
            100                 105                 110

Lys Leu Arg Ser Leu Glu Lys Val Leu Ile Asp Ala Leu Arg Pro Glu
        115                 120                 125

Val Thr Trp Val Val Leu Ala Gly Ser Leu Pro Pro Gly Ala Pro Val
    130                 135                 140

Asp Trp Tyr Ala Arg Leu Thr Ala Leu Ile His Ser Ala Arg Pro Asp
145                 150                 155                 160

Val Arg Val Ala Val Asp Thr Ser Asp Lys Pro Leu Met Ala Leu Gly
                165                 170                 175

Glu Ser Leu Asp Thr Pro Gly Ala Ala Pro Asn Leu Ile Lys Pro Asn
            180                 185                 190

Gly Leu Glu Leu Gly Gln Leu Ala Asn Thr Asp Gly Glu Glu Leu Glu
        195                 200                 205

Ala Arg Ala Ala Gln Gly Asp Tyr Asp Ala Ile Ile Ala Ala Ala Asp
    210                 215                 220

Val Leu Val Asn Arg Gly Ile Glu Gln Val Leu Val Thr Leu Gly Ala
225                 230                 235                 240

Ala Gly Ala Val Leu Val Asn Ala Glu Gly Ala Trp Thr Ala Thr Ser
                245                 250                 255

Pro Lys Ile Asp Val Val Ser Thr Val Gly Ala Gly Asp Cys Ala Leu
            260                 265                 270

Ala Gly Phe Val Met Ala Arg Ser Gln Lys Lys Thr Leu Glu Glu Ser
        275                 280                 285

Leu Leu Asn Ala Val Ser Tyr Gly Ser Thr Ala Ser Leu Pro Gly
    290                 295                 300

Thr Thr Ile Pro Arg Pro Asp Gln Leu Ala Thr Ala Gly Ala Thr Val
305                 310                 315                 320

Thr Gln Val Lys Gly Leu Lys Glu Ser Ala

```
                       325                 330

<210> SEQ ID NO 5
<211> LENGTH: 27
<212> TYPE: DNA
<213> ORGANISM: Corynebacterium glutamicum

<400> SEQUENCE: 5
cttctagacc cgaccacaac tttcagg                                        27

<210> SEQ ID NO 6
<211> LENGTH: 29
<212> TYPE: DNA
<213> ORGANISM: Corynebacterium glutamicum

<400> SEQUENCE: 6
agaagcttgc caggtgtatc caagctctc                                      29
```

PROCESS FOR THE PREPARATION OF AMINO ACIDS BY USING CORYNEFORM BACTERIA WITH ATTENUATED 1-PHOSPHOFRUCTOKINASE ACTIVITY

BACKGROUND OF THE INVENTION

The invention provides a process for the preparation of L-amino acids, in particular L-lysine, by using coryneform bacteria in which the pfkA gene coding for 6-phosphofructokinase and/or the pfkB gene coding for 1-phosphofructokinase are/is attenuated. All references cited herein are expressly incorporated by reference. Incorporation by reference is also designated by the term "I.B.R." following any citation.

L-amino acids, in particular L-lysine, find application in human medicine and in the pharmaceutical industry, in the food industry and, quite especially, in animal nutrition.

It is known that amino acids are prepared by fermentation of strains of coryneform bacteria, in particular *Corynebacterium glutamicum*. On account of its great importance, work on improving the production process is constantly in progress. Improvements to the process may concern measures pertaining to fermentation technology, such as, for example, stirring and provision with oxygen, or the composition of the nutrient media, such as, for example, the sugar concentration during fermentation, or the reprocessing into product-form by, for example, ion-exchange chromatography, or the intrinsic output properties of the micro-organism itself.

With a view to improving the output properties of these micro-organisms, methods of mutagenesis, selection and mutant selection are adopted. In this way, strains are obtained that are resistant to antimetabolites such as, for example, the lysine analogue S-(2-aminoethyl)cysteine or that are auxotrophic in respect of metabolites of regulatory significance and that produce L-amino acids.

Methods pertaining to recombinant DNA technology have also been employed for a number of years for the improvement of strains of *Corynebacterium glutamicum* producing L-amino acid, by individual amino-acid-biosynthesis genes being amplified and by the effect on the production of L-amino acid being investigated.

The invention provides improved processes for the fermentative preparation of L-amino acids, in particular L-lysine, by using coryneform bacteria.

BRIEF SUMMARY OF THE INVENTION

When mention is made in the following of L-amino acids or amino acids, these expressions are intended to mean one or more amino acids, including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is particularly preferred.

When mention is made in the following of L-lysine or lysine, these expressions are intended to mean not only the bases but also the salts such as, for example, lysine monohydrochloride or lysine sulfate.

The invention provides a process for the fermentative preparation of L-amino acids by using coryneform bacteria in which at least the nucleotide sequence coding for 6-phosphofructokinase and/or the nucleotide sequence coding for 1-phosphofructokinase are/is attenuated, in particular switched off or expressed at a low level.

This invention further provides a process for the fermentative preparation of L-amino acids in which the following steps are implemented:

a) fermentation of the coryneform bacteria producing the L-amino acid, in which at least the nucleotide sequence coding for 6-phosphofructokinase and/or the nucleotide sequence coding for 1-phosphofructokinase are/is attenuated, in particular switched off or expressed at a low level;

b) enrichment of the L-amino acids in the medium or in the cells of the bacteria; and c) isolation of the desired L-amino acids, whereby constituents of the fermentation broth and/or of the biomass optionally remain in the end product in proportions or in their total quantities.

BRIEF DESCRIPTION OF THE FIGURES

FIG. 1: map of the plasmid pXK99Emob,

FIG. 2: map of the plasmid pXK99EmobpfkB.

The abbreviations and designations that are used have the following significance.

| | |
|---|---|
| Kan: | kanamycin-resistance gene aph(3')-IIa from *Escherichia coli* |
| HindIII | cleavage site of the restriction enzyme HindIII |
| NcoI | cleavage site of the restriction enzyme NcoI |
| XbaI | cleavage site of the restriction enzyme XbaI |
| RP4-mob | RP4 mobilization site |
| Ptrc | trc promoter |
| T1 | termination region T1 |
| T2 | termination region T2 |
| LacIq | lacIq repressor of the lac operon of *Escherichia coli* |
| OriV | replication origin ColE1 from *E. coli* |
| PfkB | cloned region of the pfkB gene |

DETAILED DESCRIPTION OF THE INVENTION

The strains that are employed preferably already produce L-amino acids, in particular L-lysine, before the attenuation of the pfkA gene coding for 6-phosphofructokinase and/or of the pfkB gene coding for 1-phosphofructokinase.

Preferred embodiments are to be found in the Claims.

The term 'attenuation' in this context describes the diminution or switching-off of the intracellular activity of one or more enzymes (proteins) in a micro-organism that are coded by the corresponding DNA, by use being made, for example, of a weak promoter or by use being made of a gene or allele that codes for a corresponding enzyme with a low activity or that inactivates the corresponding gene or enzyme (protein) and by these measures optionally being combined.

By virtue of the measures of attenuation, the activity or concentration of the corresponding protein is lowered in general to 0 to 75%, 0 to 50%, 0 to 25%, 0 to 10% or 0 to 5% of the activity or concentration of the wild-type protein or of the activity or concentration of the protein in the initial micro-organism.

The micro-organisms that are the subject-matter of the present invention are able to produce amino acids from glucose, saccharose, lactose, fructose, maltose, molasses, starch, cellulose or from glycerin and ethanol. It may be a question of representatives of coryneform bacteria, in particular of the genus *Corynebacterium*. In the case of the genus *Corynebacterium*, in particular the species *Corynebacterium glutamicum* should be mentioned, which is known amongst experts for its ability to produce L-amino acids.

Suitable strains of the genus *Corynebacterium*, in particular of the species *Corynebacterium glutamicum*, are especially the known wild-type strains

*Corynebacterium glutamicum* ATCC13032

*Corynebacterium acetoglutamicum* ATCC15806

*Corynebacterium acetoacidophilum* ATCC13870

*Corynebacterium melassecola* ATCC17965

*Corynebacterium thermoaminogenes* FERM BP-1539

*Brevibacterium flavum* ATCC14067

*Brevibacterium lactofermentum* ATCC13869 and

*Brevibacterium divaricatum* ATCC14020 and mutants and strains prepared therefrom that produce L-amino acids, such as, for example, the L-lysine-producing strains

*Corynebacterium glutamicum* FERM-P 1709

*Brevibacterium flavum* FERM-P 1708

*Brevibacterium lactofermentum* FERM-P 1712

*Corynebacterium glutamicum* FERM-P 6463

*Corynebacterium glutamicum* FERM-P 6464 and

*Corynebacterium glutamicum* DSM 5715.

It has been found that coryneform bacteria produce L-amino acids in improved manner after attenuation of the gene coding for 6-phosphofructokinase (EC: 2.7.1.11) and/or of the gene coding for 1-phosphofructokinase (EC 2.7.1.56).

The nucleotide sequence of the gene coding for 6-phosphofructokinase of *Corynebacterium glutamicum* can be gathered from patent application WO 01/00844 I.B.R. under Identification Code RXA00206 as SEQ ID No. 53.

The nucleotide sequence of the gene coding for 1-phosphofructokinase of *Corynebacterium glutamicum* can be gathered from patent application WO 01/00844 I.B.R. under Identification Code RXA01882 as SEQ ID No. 57.

The nucleotide sequences are also deposited in the gene bank under Accession Numbers AX064927 and AX064931, respectively.

The claimed nucleotide sequences of the genes coding for 1-phosphofructokinase and for 6-phosphofructokinase, represented in SEQ ID No. 3 and SEQ ID No. 1, respectively, are elongated in comparison with the sequences known from the state of the art by, in each instance, preferably up to 700 base-pairs in front of the start codon and behind the stop codon of the gene.

The elongations in comparison with the sequence known from the state of the art consist in SEQ ID No. 3 of the base-pairs 1 to 508 and 1684 to 2234, respectively.

In SEQ ID No. 1 the elongations in comparison with the sequence known from the state of the art consist of the base-pairs 1 to 531 and 1621 to 2160, respectively.

The amino-acid sequences of the associated gene products are represented in SEQ ID No. 4 and SEQ ID No. 2, respectively.

It has been found that processes for attenuation that are known as such can be employed particularly successfully with the aid of the elongated sequences that are made available in this way.

Such a process is the method of gene replacement. With this method, a mutation such as, for example, a deletion, an insertion or base-exchange in the gene of interest is produced in vitro. The allele that is produced is, in turn, cloned into a vector that is non-replicative in respect of *C. glutamicum* and said vector is subsequently converted by transformation or conjugation into the desired host of *C. glutamicum*. After homologous recombination by means of a first cross-over event bringing about integration and by means of a suitable second cross-over event in the target gene or in the target sequence bringing about an excision, the incorporation of the mutation or of the allele is obtained. This method was used in EP 1 156 115 A I.B.R., for example, in order to switch off the secG gene of *C. glutarnicum*.

The elongation of the sequences that are employed is not restricted to 600 base-pairs in front of the start codon and behind the stop codon. It preferably lies within the range from 300 to 700 base-pairs, but it may also amount to up to 800 base-pairs. The elongations may also contain different quantities of base-pairs.

The sequences, described in the stated passages, coding for 6-phosphofructokinase or 1-phosphofructokinase can be used in accordance with the invention. Moreover, use can be made of alleles of 6-phosphofructokinase or 1-phosphofructokinase that arise from the degenerate nature of the genetic code or as a result of functionally neutral sense mutations.

With a view to achieving an attenuation, either the expression of the gene coding for 6-phosphofructokinase and/or of the gene coding for 1-phosphofructokinase or the catalytic properties of the gene products can be lowered or switched off. Both measures are optionally combined.

The gene expression can be reduced by suitable culturing or by genetic modification (mutation) of the signal structures of gene expression. Signal structures of gene expression are, for example, repressor genes, activator genes, operators, promoters, attenuators, ribosome binding sites, the start codon and terminators. Data relating to this can be found by a person skilled in the art in, for example, patent application WO 96/15246, in Boyd and Murphy (Journal of Bacteriology 170: 5949 (1988)) I.B.R., in Voskuil and Chambliss (Nucleic Acids Research 26: 3548 (1998), in Jensen and Hammer (Biotechnology and Bioengineering 58: 191 (1998)) I.B.R., in Pátek et al. (Microbiology 142: 1297 (1996)) I.B.R. and in known textbooks on genetics and molecular biology such as, for example, the textbook by Knippers (*Molekulare Genetik*, 6$^{th}$ Edition, Georg Thieme Verlag, Stuttgart, Germany, 1995) I.B.R. or in that by Winnacker (*Gene und Klone*, VCH Verlagsgesellschaft, Weinheim, Germany, 1990) I.B.R.

Mutations that lead to a change in or a lowering of the catalytic properties of enzyme proteins are known from the state of the art; by way of examples, mention may be made of the papers by Qiu and Goodman (Journal of Biological Chemistry 272: 8611–8617 (1997)) I.B.R., Sugimoto et al. (Bioscience Biotechnology and Biochemistry 61: 1760–1762 (1997)) I.B.R. and Möckel (*Die Threonindehydratase aus Corynebacterium glutamicum: Aufhebung der allosterischen Regulation und Struktur des Enzyms*, Berichte des Forschungszentrums Jülichs, Jül-2906, ISSN09442952, Jülich, Germany, 1994 I.B.R.). Synoptic accounts can be gathered from known textbooks on genetics and molecular biology such as, for example, that by Hagemann (*Allgemeine Genetik*, Gustav Fischer Verlag, Stuttgart, 1986) I.B.R.

Transitions, transversions, insertions and deletions enter into consideration by way of mutations. Depending on the effect of the amino-acid exchange on the enzyme activity, one speaks of missense mutations or nonsense mutations. Insertions or deletions of at least one base-pair in a gene lead to frame-shift mutations, as a consequence of which false amino acids are incorporated or the translation terminates prematurely. Deletions of several codons typically lead to a complete loss of enzyme activity. Instructions for the generation of mutations of such a type pertain to the state of the art and can be gathered from known textbooks on genetics and molecular biology such as, for example, the textbook by Knippers (*Molekulare Genetik, 6th* Edition, Georg Thieme Verlag, Stuttgart, Germany, 1995) I.B.R., that by Winnacker (*Gene und Klone*, VCH Verlagsgesellschaft, Weinheim, Germany, 1990) or that by Hagemann (*Allgemeine Genetik*, Gustav Fischer Verlag, Stuttgart, 1986) I.B.R.

Customary methods for mutating genes of *C. glutamicum* are the methods of gene disruption and of gene replacement described by Schwarzer and Pühler (Bio/Technology 9, 84–87 (1991)) I.B.R.

In the case of the method of gene disruption, a central part of the coding region of the gene of interest is cloned into a plasmid vector that is able to replicate in a host (typically *E. coli*) but not in *C. glutamicum*. By way of vectors, pSUP301 (Simon et al., Bio/Technology 1, 784–791 (1983) I.B.R.), pK18mob or pK19mob (Schäfer et al., Gene 145, 69–73 (1994) I.B.R.), pK18mobsacB or pK19mobsacB (Jäger et al., Journal of Bacteriology 174: 5462–65 (1992) I.B.R.), pGEM-T (Promega corporation, Madison, Wis., USA), pCR2.1-TOPO (Shuman (1994), Journal of Biological Chemistry 269:32678–84 I.B.R.; U.S. Pat. No. 5,487,993 I.B.R.), pCR® Blunt (Invitrogen, Groningen, Netherlands; Bernard et al., Journal of Molecular Biology, 234: 534–541 (1993) I.B.R.) or pEM1 (Schrumpf et al, 1991, Journal of Bacteriology 173:4510–4516 I.B.R.), for example, enter into consideration. The plasmid vector, which contains the central part of the coding region of the gene, is subsequently converted by conjugation or transformation into the desired strain of *C. glutamicum*. The method of conjugation is described, for example, in Schäfer et al. (Applied and Environmental Microbiology 60, 756–759 (1994)) I.B.R. Methods for transformation are described, for example, in Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a cross-over event, the coding region of the gene in question is interrupted by the vector sequence, and two incomplete alleles are obtained, from each of which the 3'-end or the 5'-end is missing. This method was used, for example, by Fitzpatrick et al. (Applied Microbiology and Biotechnology 42, 575–580 (1994)) I.B.R. for the purpose of switching off the recA gene of *C. glutamicum*.

In the case of the method of gene replacement, a mutation such as, for example, a deletion, an insertion or a base-exchange in the gene of interest is produced in vitro. The allele that is produced is, in turn, cloned into a vector that is non-replicative in respect of *C. glutamicum* and said vector is subsequently converted by transformation or conjugation into the desired host of *C. glutamicum*. After homologous recombination by means of a first cross-over event bringing about integration and by means of a suitable second cross-over event in the target gene or in the target sequence bringing about an excision, the incorporation of the mutation or of the allele is obtained. This method was used, for example, by Peters-Wendisch et al. (Microbiology 144, 915–927 (1998)) I.B.R., in order to switch off the pyc gene of *C. glutamicum* by a deletion.

In this way a deletion, an insertion or a base-exchange can be incorporated into the gene coding for 6-phosphofructokinase and/or the gene coding for 1-phosphofructokinase.

In addition, for the production of L-amino acids it can be advantageous, in addition to the attenuation of the gene coding for 6-phosphofructokinase and/or of the gene coding for 1-phosphofructokinase, to enhance, in particular to overexpress, one or more enzymes of the respective biosynthetic pathway, of glycolysis, of anaplerotic reactions, of the citric-acid cycle, of the pentose-phosphate cycle, of the export of amino acid and optionally regulatory proteins.

The term 'enhancement' or in this context describes the increase in the intracellular activity of one or more enzymes or proteins in a micro-organism which are coded by the corresponding DNA by, for example, the copy-number of the gene or genes being increased, by use being made of a strong promoter or a gene that codes for a corresponding enzyme or protein with a high activity and by optionally combining these measures.

By virtue of the measures of enhancement, in particular overexpression, the activity or concentration of the corresponding protein is increased in general by at least 10%, 25%, 50%, 75%, 100%, 150%, 200%, 300%, 400% or 500%, maximally up to 1000% or 2000%, relative to that of the wild-type protein or of the activity or concentration of the protein in the initial micro-organism.

The use of endogenous genes is generally preferred. The term "endogenous genes" or "endogenous nucleotide sequences" is to be understood to mean the genes or nucleotide sequences, respectively, existing in the population of a species.

Thus, for the preparation of L-lysine, in addition to the attenuation of the gene coding for 6-phosphofructokinase and/or of the gene coding for 1-phosphofructokinase, one or more of the genes selected from the group comprising the gene lysC coding for a feedback-resistant aspartate kinase (Accession No. P26512, EP-B-0387527 I.B.R.; EP-A-0699759 I.B.R.; WO 00/63388 I.B.R.), the gene dapA coding for dihydrodipicolinate synthase (EP-B 0 197 335 I.B.R.), the gene gap coding for glyceraldehyde-3-phosphate dehydrogenase (Eikmanns (1992), Journal of Bacteriology 174:6076–6086 I.B.R.), simultaneously the gene pyc coding for pyruvate carboxylase (DE-A-198 31 609 I.B.R.), the gene mqo coding for malate:quinone oxidoreductase (Molenaar et al., European Journal of Biochemistry 254, 395–403 (1998) I.B.R.), the gene zwf coding for glucose-6-phosphate dehydrogenase (JP-A-09224661 I.B.R.), simultaneously the gene lysE coding for the lysine-export protein (DE-A-195 48 222 I.B.R.), the gene zwa1 coding for the zwa1 protein (DE: 19959328.0 I.B.R., DSM 13115), the gene tpi coding for triosephosphate isomerase (Eikmanns (1992), Journal of Bacteriology 174:6076–6086 I.B.R.), and the gene pgk coding for 3-phosphoglycerate kinase (Eikmanns (1992), Journal of Bacteriology 174:6076–6086 I.B.R.)

is/are enhanced, in particular overexpressed.

Moreover, for the production of amino acids, in particular L-lysine, it can be advantageous, in addition to the attenuation of the gene coding for 6-phosphofructokinase and/or of the gene coding for 1-phosphofructokinase, simultaneously to attenuate, in particular to reduce the expression of, one or more of the genes selected from the group comprising the gene pck coding for phosphoenolpyruvate carboxykinase (DE 199 50 409.1 I.B.R., DSM 13047), the gene pgi coding for glucose-6-phosphate isomerase (U.S. Ser. No. 09/396,478 I.B.R., DSM 12969), the gene poxB coding for pyruvate oxidase (DE:1995 1975.7 I.B.R., DSM 13114), the gene fda coding for fructose bisphosphate aldolase (Mol. Microbiol. 3 (11), 1625–1637 (1989) I.B.R.; gene bank Accession Number X17313) and the gene zwa2 coding for the zwa2 protein (DE: 19959327.2 I.B.R., DSM 13113).

Finally, for the production of amino acids it can be advantageous, in addition to the attenuation of the gene coding for 6-phosphofructokinase and/or of the gene coding for 1-phosphofructokinase, to exclude undesirable side reactions (Nakayama: *Breeding of Amino Acid Producing Microorganisms*, in: *Overproduction of Microbial Products*, Krumphanzl, Sikyta, Vanek (eds.), Academic Press, London, UK, 1982 I.B.R.).

The micro-organisms that are produced in accordance with the invention are likewise a subject of the invention and can be cultivated continuously or discontinuously in the batch process (batch cultivation) or in the fed-batch or repeated-fed-batch process for the purpose of producing L-amino acids. A summary of known cultivation methods is described in the textbook by Chmiel (*Bioprozesstechnik* 1. *Einführung in die Bioverfahrenstechnik* (Gustav Fischer Verlag, Stuttgart, 1991) I.B.R.) or in the textbook by Storhas (*Bioreaktoren und periphere Einrichtungen* (Vieweg Verlag, Braunschweig/Wiesbaden, 1994) I.B.R.).

The culture medium to be used has to satisfy the demands of the respective strains in suitable manner. Descriptions of culture media of various micro-organisms are contained in the manual entitled *Manual of Methods for General Bacteriology* published by the American Society for Bacteriology (Washington D.C., USA, 1981) I.B.R.

Sugar and carbohydrates such as, for example, glucose, saccharose, lactose, fructose, maltose, molasses, starch and cellulose, oils and fats such as, for example, soybean oil, sunflower oil, peanut oil and coconut oil, fatty acids such as, for example, palmitic acid, stearic acid and linoleic acid, alcohols such as, for example, glycerin and ethanol, and organic acids such as, for example, acetic acid can be used by way of carbon source. These substances can be used individually or as a mixture.

Organic nitrogenous compounds such as peptones, yeast extract, meat extract, malt extract, maize steep liquor, soybean flour and urea, or inorganic compounds such as ammonium sulfate, ammonium chloride, ammonium phosphate, ammonium carbonate and ammonium nitrate can be used by way of nitrogen source. The nitrogen sources can be used individually or as a mixture.

Phosphoric acid, potassium dihydrogenphosphate or dipotassium hydrogenphosphate or the corresponding sodium-containing salts can be used by way of phosphorus source. The culture medium must, moreover, contain salts of metals such as, for example, magnesium sulfate or iron sulfate, that are necessary for growth. Finally, essential growth substances such as amino acids and vitamins can be employed in addition to the aforementioned substances. Besides, suitable precursors can be added to the culture medium. The stated feed materials can be added to the culture in the form of a single charge or can be fed in during the cultivation in suitable manner.

With a view to controlling the pH of the culture, basic compounds such as sodium hydroxide, potassium hydroxide, ammonia or ammoniacal liquor or acidic compounds such as phosphoric acid or sulfuric acid are employed in suitable manner. With a view to controlling the formation of foam, anti-foaming agents such as, for example, fatty-acid polyglycol esters can be employed. With a view to maintaining the stability of plasmids, suitable substances acting selectively, such as antibiotics for example, can be added to the medium. In order to maintain aerobic conditions, oxygen or oxygenous gas mixtures, such as air for example, are introduced into the culture. The temperature of the culture is normally around 20° C. to 45° C. and preferably 25° C. to 40° C. The culture is continued for such time until a maximum of the desired product has formed. This objective is normally attained within a period from 10 hours to 160 hours.

Methods for the determination of L-amino acids are known from the state of the art. The analysis can be undertaken as described in Spackman et al. (Analytical Chemistry, 30, (1958), 1190 I.B.R.) by anion-exchange chromatography with subsequent ninhydrin derivation, or it can be undertaken by reversed-phase HPLC, as described in Lindroth et al. (Analytical Chemistry (1979) 51: 1167–1174 I.B.R.).

The following micro-organism was deposited in the form of pure culture on 11 Jan. 2002 in the Deutsche Sammlung für Mikroorganismen und Zellkulturen (German Collection of Micro-Organisms and Cell Cultures, DSMZ, Braunschweig, Germany):

*Escherichia coli* DH5alphamcr/pXK99EmobpfkB (=DH5αmcr/pXK99EmobpfkB) as DSM 14741.

The present invention is elucidated in more detail in the following on the basis of exemplary embodiments.

Example 1

Preparation of a Genomic Cosmid Gene Bank From *Corynebacterium glutamicum* ATCC 13032

Chromosomal DNA from *Corynebacterium glutamicum* ATCC 13032 was isolated as described in Tauch et al. (1995, Plasmid 33:168–179) I.B.R. and partially cleaved with the restriction enzyme Sau3AI (Amersham Pharmacia, Freiburg, Germany, product description Sau3AI, Code No. 27-0913-02). The DNA fragments were dephosphorylated with shrimp alkaline phosphatase (Roche Diagnostics GmbH, Mannheim, Germany, product description SAP, Code No. 1758250). The DNA of the cosmid vector Super-Cos1 (Wahl et al. (1987) Proceedings of the National Academy of Sciences USA 84:2160–2164 I.B.R.), obtained from Stratagene (La Jolla, USA, product description Super-Cos1 Cosmid Vektor Kit, Code No. 251301) was cleaved with the restriction enzyme XbaI (Amersham Pharmacia, Freiburg, Germany, product description XbaI, Code No. 27-0948-02) and likewise dephosphorylated with shrimp alkaline phosphatase.

Subsequently the cosmid DNA was cleaved with the restriction enzyme BamHI (Amersham Pharmacia, Freiburg, Germany, product description BamHI, Code No. 27-0868-04). The cosmid DNA that was treated in this way was mixed with the treated ATCC13032 DNA, and the charge was treated with T4-DNA-Ligase (Amersham Pharmacia, Freiburg, Germany, product description T4-DNA-Ligase, Code No. 27-0870-04). The ligation mixture was subsequently packaged in phages with the aid of the Gigapack II XL Packing Extracts (Stratagene, La Jolla, USA, product description Gigapack II XL Packing Extract, Code No. 200217).

With a view to infection of the *E. coli* strain NM554 (Raleigh et al. 1988, Nucleic Acid Research 16:1563–1575

I.B.R.), the cells were taken up in 10 mM MgSO$_4$ and mixed with an aliquot of the phage suspension. Infection and titration of the cosmid bank were carried out as described in Sambrook et al. (1989, Molecular Cloning: A Laboratory Manual, Cold Spring Harbor) I.B.R., whereby the cells were plated onto LB agar (Lennox, 1955, Virology, 1:190 I.B.R.) with 100 mg/l ampicillin. After incubation overnight at 37° C., recombinant single clones were selected.

Example 2

Ascertainment of the Upstream and Downstream Elongations of the Sequences of the Genes pfkA and pfkB Known From the State of the Art The cosmid DNA of a single colony was isolated with the Qiaprep Spin Miniprep Kit (Product No. 27106, Qiagen, Hilden, Germany) in accordance with the manufacturer's instructions and partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Diagnostics GmbH, Mannheim, Germany, product description SAP, Product No. 1758250). After gel-electrophoretic fractionation, isolation of the cosmid fragments was effected within the size-range from 1500 to 2000 bp with the QiaExII Gel Extraction Kit (Product No. 20021, Qiagen, Hilden, Germany I.B.R.).

The DNA of the sequencing vector pZero-1 obtained from Invitrogen (Groningen, Netherlands, product description Zero Background Cloning Kit, Product No. K2500-01 I.B.R.) was cleaved with the restriction enzyme BamHI (Amersham Pharmacia, Freiburg, Germany, product description BamHI, Product No. 27-0868-04 I.B.R.). The ligation of the cosmid fragments into the sequencing vector pZero-1 was carried out as described by Sambrook et al. (1989, Molecular Cloning: A Laboratory Manual, Cold Spring Harbor I.B.R.), whereby the DNA mixture was incubated overnight with T4-Ligase (Pharmacia Biotech, Freiburg, Germany). This ligation mixture was subsequently electroporated into the *E. coli* strain DH5αMCR (Grant, 1990, Proceedings of the National Academy of Sciences U.S.A., 87:4645–4649 I.B.R.) (Tauch et al. 1994, FEMS Microbiol Letters, 123:343–7 I.B.R.) and plated onto LB agar (Lennox, 1955, Virology, 1:190 I.B.R.) with 50 mg/l Zeocin.

The plasmid preparation of the recombinant clones was undertaken with a Biorobot 9600 (Product No. 900200, Qiagen, Hilden, Germany). Sequencing was effected in accordance with the dideoxy chain-termination method of Sanger et al. (1977, Proceedings of the National Academy of Sciences U.S.A., 74:5463–5467) I.B.R. with modifications in accordance with Zimmermann et al. (1990, Nucleic Acids Research, 18:1067) I.B.R. Use was made of the "RR dRhodamin Terminator Cycle Sequencing Kit" manufactured by PE Applied Biosystems (Product No. 403044, Weiterstadt, Germany). Gel-electrophoretic fractionation and analysis of the sequencing reaction were undertaken in a "Rotiphorese NF Acrylamid/Bisacrylamid" gel (29:1) (Product No. A124.1, Roth, Karlsruhe, Germany I.B.R.) with an "ABI Prism 377" sequencer manufactured by PE Applied Biosystems (Weiterstadt, Germany).

The raw sequence data obtained were subsequently processed by applying the Staden program package (1986, Nucleic Acids Research, 14:217–231 I.B.R.) Version 97-0. The individual sequences of the pZero1 derivatives were assembled into a coherent contig. The computer-aided coding-region analysis was produced with the program XNIP (Staden, 1986, Nucleic Acids Research, 14:217–231 I.B.R.). Further analyses can be carried out with the "BLAST search program" (Altschul et al., 1997, Nucleic Acids Research, 25:3389–3402 I.B.R.) against the non-redundant databank of the "National Center for Biotechnology Information" (NCBI, Bethesda, Md., USA) I.B.R.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

The known nucleotide sequences of the genes pfkA and pfkB that are extended by the upstream and downstream elongations obtained in this way are represented in SEQ ID No. 1 and SEQ ID No. 3.

Example 3

Preparation of the Expression Vector pXK99EmobpfkB for IPTG-induced Expression of the pfkB Gene in *C. glutamicum*

3.1 Cloning of the pfkB gene

Chromosomal DNA is isolated from the strain ATCC 13032 in accordance with the method of Eikmanns et al. (Microbiology 140: 1817–1828 (1994)) I.B.R. On the basis of the known sequence of the pfkB gene for *C. glutamicum* the following oligonucleotides for the polymerase chain reaction are selected:

```
                                            SEQ ID NO:5
pfkB for:
5'-CT TCT AGA-CCC GAC CAC AAC TTT CAG G-3'

SEQ ID NO:6
pfkBint int:
5'-AG AAG CTT-GCC AGG TGT ATC CAA GCT CTC-3'
```

In this connection the primers are selected in such a way that the amplified fragment contains the incomplete gene, beginning with the native ribosome binding site without promoter region, as well as the anterior region of the pfkB gene. In addition, the primer pfkB for contains the sequence for the cleavage site of the restriction endonuclease XbaI, and the primer pfkB int contains the sequence for the cleavage site of the restriction endonuclease HindIII, which are marked by underlining in the nucleotide sequences represented above.

The primers that are represented are synthesized by MWG-Biotech AG (Ebersberg, Germany), and the PCR reaction is carried out in accordance with the standard PCR method of Innis et al. (PCR Protocols. A Guide to Methods and Applications, 1990, Academic Press) I.B.R. with Pwo polymerase produced by Roche Diagnostics GmbH (Mannheim, Germany). With the aid of the polymerase chain reaction the primers enable the amplification of a 594-bp DNA fragment that bears the incomplete pfkB gene including the native ribosome binding site.

The 594-bp pfkB fragment is cleaved with the restriction endonucleases XbaI and HindIII and is subsequently isolated from the agarose gel with the QiaExII Gel Extraction Kit (Product No. 20021, Qiagen, Hilden, Germany I.B.R.).

3.2 Construction of the expression vector pXK99Emob

The IPTG-inducible expression vector pXK99Emob is constructed in accordance with the state of the art. The vector is based on the *Escherichia coli* expression vector pTRC99A (Amann et al., Gene 69: 301–315 (1988) I.B.R.) and contains the trc promoter which is inducible by addition of the lactose derivative IPTG (isopropyl-β-D-thiogalactopyranoside), the termination regions T1 and T2, the replication origin ColE1 from *E. Coli*, the lacI$^q$ gene (repressor of the lac operon of *E.coli*), a multiple cloning site (mcs) (Norrander, J. M. et al. Gene 26, 101–106 (1983) I.B.R.), the kanamycin-resistance gene aph(3')-IIa from *E. coli* (Beck et al. (1982), Gene 19: 327–336 I.B.R.) and the RP4 mobilization site from the cloning vector pK18mobsacB (Schäfer et al., Gene 14: 69–73 (1994) I.B.R.).

It has been found that the vector pXK99Emob is quite especially suitable for regulating the expression of a gene, in particular for bringing about the attenuated expression in coryneform bacteria. The vector pXK99Emob is an *E. coli* expression vector and can be employed in *E. coli* for the enhanced expression of a gene.

Since the vector cannot replicate independently in coryneform bacteria, it is preserved in the cell only when it integrates into the chromosome. The peculiarity of this vector in this connection is the use for the regulated expression of a gene after cloning of a gene segment from the anterior region of the corresponding gene into the vector, containing the start codon and the native ribosome binding site, and after subsequent integration of the vector in coryneform bacteria, in particular *C. glutamicum*. By addition of metered amounts of IPTG to the nutrient medium the gene expression is regulated. In this connection, quantities from 0.5 μM up to 10 μM IPTG bring about a very weak expression of the corresponding gene, and quantities from 10 μM up to 100 μM bring about a slightly attenuated to normal expression of the corresponding gene.

The constructed *E. coli* expression vector pXK99Emob is transferred by means of electroporation (Tauch et al. 1994, FEMS Microbiol Letters, 123: 343–347 I.B.R.) into *E. coli* DH5αmcr (Grant, 1990, Proceedings of the National Academy of Sciences U.S.A., 87:4645–4649 I.B.R.). Selection of the transformants is undertaken on LB agar (Sambrook et al., Molecular Cloning: A Laboratory Manual, 2$^{nd}$ Ed., Cold Spring Harbor Laboratory Press, Cold Spring Harbor, N.Y., 1989 I.B.R.) that has been supplemented with 50 mg/l kanamycin.

Plasmid DNA is isolated from a transformant in accordance with the customary methods (Peters-Wendisch et al., 1998, Microbiology, 144, 915–927 I.B.R.), is cut with the restriction endonuclease NcoI, and the plasmid is examined by subsequent agarose-gel electrophoresis.

The plasmid construct that is obtained in this way is designated as pXK99Emob (FIG. 1). The strain that is obtained by electroporation of the plasmid pXK99Emob into the *E. coli* strain DH5αmcr is called *E. coli* DH5αmcr/pXK99Emob.

3.3 Cloning of the pfkB fragment into the *E. coli* expression vector pXK99Emob By way of vector, use is made of the *E. coli* expression vector pXK99Emob described in Example 3.2. DNA of this plasmid is cleaved completely with the restriction enzymes XbaI and HindIII and is subsequently dephosphorylated with shrimp alkaline phosphatase (Roche Diagnostics GmbH, Mannheim, Germany, product description SAP, Product No. 1758250 I.B.R.).

The approximately 580-bp pfkB fragment described in Example 3.1, which is obtained by means of PCR and cleaved with the restriction endonucleases XbaI and HindIII, is mixed with the prepared vector pXK99Emob, and the charge is treated with T4-DNA-Ligase (Amersham Pharmacia, Freiburg, Germany, product description T4-DNA-Ligase, Code No. 27-0870-04 I.B.R.). The ligation charge is transformed into the *E. coli* strain DH5αmcr (Hanahan, In: DNA Cloning. A Practical Approach, Vol. I, IRL Press, Oxford, Washington D.C., USA I.B.R.). Selection of plasmid-bearing cells is undertaken by plating the transformation charge onto LB agar (Lennox, 1955, Virology, 1:190 I.B.R.) with 50 mg/l kanamycin. After incubation overnight at 37° C., recombinant individual clones are selected. Plasmid DNA is isolated from a transformant with the Qiaprep Spin Miniprep Kit (Product No. 27106, Qiagen, Hilden, Germany I.B.R.) in accordance with the manufacturer's instructions and is cleaved with the restriction enzymes XbaI and HindIII, in order to examine the plasmid by subsequent agarose-gel electrophoresis. The plasmid that is obtained is called pXK99EmobpfkB. It is represented in FIG. 2.

Example 4

Integration of the Vector pXK99EmobpfkB Into the Genome of the *C. glutamicum* Strain DSM5715

The vector pXK99EmobpfkB named in Example 3 is electroporated into the strain *C. glutamicum* DSM5715 in accordance with the electroporation method of Tauch et al. (1989 FEMS Microbiology Letters 123: 343–347) I.B.R. The vector cannot replicate independently in DSM5715 and is preserved in the cell only when it has integrated into the chromosome. Selection of clones with integrated pXK99EmobpfkB is undertaken by plating the electroporation charge onto LB agar (Sambrook et al., Molecular Cloning: A Laboratory Manual, 2$^{nd}$ Ed., Cold Spring Harbor, N.Y., 1989 I.B.R.) that has been supplemented with 15 mg/l kanamycin and IPTG (1 mM).

A selected kanamycin-resistant clone that has inserted the plasmid pXK99EmobpfkB named in Example 3 within the chromosomal pfkB gene of DSM5715 is designated as DSM5715::pXK99EmobpfkB.

Example 5

Preparation of Lysine

The *C. glutamicum* strain DSM5715::pCXK99EmobpfkB obtained in Example 4 is cultured in a nutrient medium that is suitable for the production of lysine, and the lysine content in the supernatant of the culture is determined. Addition of IPTG results in an attenuated expression of the pfkB gene, regulated by the trc promoter.

To this end, the strain is firstly incubated for 24 hours at 33° C. on agar plate with the appropriate antibiotic (brain/heart agar with kanamycin (25 mg/l) and IPTG (10 μM)). Starting from this agar-plate culture, a preculture is inoculated (10 ml medium in a 100-ml Erlenmeyer flask). The complete medium Cg III is used as medium for the preculture.

| Medium Cg III | |
|---|---|
| NaCl | 2.5 g/l |
| Bacto-peptone | 10 g/l |
| Bacto-yeast extract | 10 g/l |
| Glucose (autoclaved separately) | 2% (w/v) |
| The pH value was adjusted to pH 7.4 | |

To this medium there are added kanamycin (25 mg/l) and IPTG (10 μM). The preculture is incubated on the shaker for 16 hours at 33° C. at 240 rpm. A main culture is inoculated from this preculture, so that the initial OD (660 nm) of the main culture amounts to 0.1. The medium MM is used for the main culture.

To this medium there were added kanamycin (25 mg/l) and IPTG (10 μM). The preculture was incubated on the shaker for 16 hours at 33° C. at 240 rpm. The OD (660) of the preculture amounted to 14.7. 68 μl from this preculture were inoculated into a main culture, so that the initial OD (660 nm) of the main culture amounted to 0.1. By virtue of the transfer of IPTG-containing medium from the preculture, the IPTG concentration in the main culture amounted to about 0.07 μM/l. The medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |

| -continued | |
|---|---|
| Medium MM | |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamin * HCl (sterilized by filtration) | 0.2 mg/l |
| Leucine (sterilized by filtration) | 0.1 g/l |
| $CaCO_3$ | 25 g/l |

CSL, MOPS and the salt solution are adjusted to pH 7 with ammoniacal liquor and are autoclaved. Subsequently the sterile substrate and vitamin solutions are added, as well as the dry-autoclaved $CaCO_3$.

Culturing is effected in 10 ml volumes in a 100-ml Erlenmeyer flask with baffles. Kanamycin (25 mg/l) is added. Culturing is effected at 33° C. and at 80% atmospheric moisture.

After 48 hours the OD at a measuring wavelength of 660 nm is ascertained with a Biomek 1000 (Beckmann Instruments GmbH, Munich). The quantity of lysine that is formed is determined with an amino-acid analyzer manufactured by Eppendorf-BioTronik (Hamburg, Germany) by ion-exchange chromatography and post-column derivation with detection of ninhydrin.

The result of the experiment is represented in Table 1.

TABLE 1

| Strain | OD (660 nm) | Lysine HCl g/l |
|---|---|---|
| DSM5715 | 12.2 | 15.31 |
| DSM5715::pXK99EmobpfkB | 7.8 | 16.89 |

This application claims priority to German Priority Document Application No. 101 12 992.0, filed on Mar. 17 26, 2001. The German Priority Document is hereby incorporated by reference in its entirety.

What is claimed is:

1. A process for the fermentative preparation of L-amino acids in *Corynebacterium glutamicum* bacteria, comprising:
   a) fermenting the bacteria, in which at least the gene encoding 1-phosphofructokinase is eliminated by a method of mutagenesis selected from the group consisting of insertion of at least one base pair, deletion of at least one base pair, and transition or transversion mutagenesis with incorporation of a nonsense mutation, in a medium and for a time suitable for the formation of the L-amino acids; and
   b) accumulating the produced L-amino acids in medium or in the cells of the bacteria.

2. The method according to claim 1, further comprising:
   c) isolating the L-amino acid.

3. The method according to claim 2, wherein the medium includes a fermentation broth and constituents of the fermentation broth remain in the end product in some proportion of their original quantity.

4. The method according to claim 2, wherein constituents of a biomass of the cells remain in the end product in some proportion of their original quantity.

5. The method according to claim 1, wherein the L-amino acids are L-lysine.

6. The method according to claim 1, wherein the bacteria being fermented further comprise one or more overexpressed genes selected from the group consisting of:
   the gene that encodes aspartate kinase,
   the gene that encodes dihydrodipicolinate synthase,
   the gene that encodes glyceraldehyde-3-phosphate dehydrogenase,
   the gene that encodes pyruvate carboxylase,
   the gene that encodes malate:quinone oxidoreductase,
   the gene that encodes glucose-6-phosphate dehydrogenase,
   the gene that encodes the lyseE protein,
   the gene that encodes the zwa1 protein,
   the gene that encodes triosephosphate isomerase, and
   the gene that encodes 3-phosphoglycerate kinase.

7. The method according to claim 1, wherein the bacteria being fermented have expression of one or more genes, endogenous to said bacteria being eliminated, wherein the one or more genes is/are selected from the group consisting of:
   the gene that encodes phosphoenolpyruvate carboxykinase,
   the gene that encodes glucose-6-phosphate isomerase,
   the gene that encodes pyruvate oxidase,
   the gene that encodes fructose bisphosphate aldolase, and
   the gene that encodes the zwa2 protein, and
   wherein said elimination is achieved by a method of mutagenesis selected from the group consisting of insertion of at least one base pair, deletion of at least one base pair, and transition or transversion mutagenesis with incorporation of a nonsense mutation.

8. The method according to claim 1, wherein said gene encoding 1-phosphofructokinase is a polynucleotide encoding a protein comprising the amino acid sequence of SEQ ID NO: 4.

9. The method according to claim 8, wherein said polynucleotide comprises the nucleotide sequence of nucleotides 609 to 1598 of SEQ ID NO: 3.

\* \* \* \* \*